United States Patent
Hüglin et al.

(10) Patent No.: US 7,381,423 B2
(45) Date of Patent: *Jun. 3, 2008

(54) USE OF NANODISPERSIONS IN COSMETIC END FORMULATIONS

(75) Inventors: Dietmar Hüglin, Weil am Rhein (DE); Joachim Friedrich Röding, Badenweiler (DE); Andreas Werner Supersaxo, Baar (CH); Hans Georg Weder, Rüschlikon (CH)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 506 days.

This patent is subject to a terminal disclaimer.

(21) Appl. No.: 11/103,208

(22) Filed: Apr. 11, 2005

(65) Prior Publication Data

US 2005/0191330 A1    Sep. 1, 2005

Related U.S. Application Data

(63) Continuation-in-part of application No. 10/016,903, filed on Dec. 14, 2001, now Pat. No. 7,008,638, which is a continuation of application No. 09/306,005, filed on May 6, 1999, now abandoned.

(30) Foreign Application Priority Data

May 11, 1998 (EP) ................... 98810421

(51) Int. Cl.
*A61K 9/127* (2006.01)
*A61K 7/00* (2006.01)

(52) U.S. Cl. ............ 424/450; 424/401; 264/4.1; 264/4.3; 264/4.6; 514/937; 514/938

(58) Field of Classification Search ........... 424/450, 424/401; 264/4.1, 4.3; 514/937–943
See application file for complete search history.

(56) References Cited

U.S. PATENT DOCUMENTS

| 5,658,898 | A | 8/1997 | Weder et al. ........ 514/211 |
| 5,858,410 | A | 1/1999 | Muller et al. ........ 424/489 |
| 6,039,936 | A | 3/2000 | Restle et al. ........ 424/70.1 |
| 2004/0266725 | A1 | 12/2004 | Inohara et al. ........ 514/54 |

FOREIGN PATENT DOCUMENTS

| CA | 2067754 | 2/1992 |
| CA | 2238263 | 6/1997 |
| CA | 2217039 | 5/1998 |
| EP | 0349150 | 1/1990 |
| EP | 0711557 | 5/1996 |
| EP | 0852941 | 7/1998 |
| WO | 96/37192 | 11/1996 |
| WO | 97/03642 | 2/1997 |
| WO | 97/21428 | 6/1997 |

OTHER PUBLICATIONS

Patent Abstracts of Japan vol. 97, No. 007, JP09059145, (1997).
Abstracts for EP 0852941 (1998).
Information Sheet for APV Manton Gaulin Homogeniser (2 stage) 400MC7-5TPS from ProcessPlant.com.

*Primary Examiner*—Gollamudi Kishore
(74) *Attorney, Agent, or Firm*—Mervin G. Wood

(57) ABSTRACT

A description is given of the use of a nanodispersion, which comprises
(a) a membrane-forming molecule,
(b) a coemulsifier and
(c) a lipophilic component,
in cosmetic end formulation, which nanodispersion is obtainable by
(α) mixing the components (a), (b) and (c) until a homogeneous clear liquid is obtained, and
(β) adding the liquid obtained in, step (α) to the water phase of the cosmetic end formulations, steps (α) and (β) being carried out without any additional supply of energy.

The nanodispersions used according to this invention can be easily prepared and are suitable as carrier systems for a very wide range of cosmetic active agents and oil-soluble dyes.

22 Claims, No Drawings

USE OF NANODISPERSIONS IN COSMETIC END FORMULATIONS

This is a continuation-in-part of application Ser. No. 10/016,903, filed Dec. 14, 2001, now U.S. Pat. No. 7,008,638, which is a continuation of application Ser. No. 09/306,005 filed May 6, 1999, abandoned.

The present invention relates to the use of specific nanodispersions in cosmetic end formulations, to cosmetic end formulations comprising said nanodispersions and to the different cosmetic uses of these end formulations.

Cosmetic preparations comprising, in addition to the basic substances responsible for forming the cosmetic formulations, other functional active agents. These are added to the cosmetic base formulations and are used, for example, for treatment, protection, colouring, cleansing, disinfection, for moisturising skin and for regenerating and activating skin or hair. In order for these substances to have an effect at the desired site, they must be transported to the respective site, for example to the skin surface, mucosae, nails, dental enamel or hair, but also to the epidermal and dermal areas of the skin, by means of so-called carrier and transport vehicles (carrier systems). To this purpose, many cosmetic active agents, for example water-soluble vitamins, the amino acid group or the water-soluble melanines, are encapsulated in liposomes. Owing to the properties of the liposomes, lipophilic substances can be encapsulated only in minor amounts in the lipophilic areas of the liposome membrane. For this reason, so-called nanoemulsions, also called nanoparticles, are used for such compounds, e.g. fat-soluble vitamins.

Owing to the physical and chemical properties of the membranes and the membrane-forming molecules, the use of said carrier systems in conventional cosmetic formulations is severely limited.

Conventionally structured membranes are highly susceptible to amphiphilic substances, such as ionogenic or non-ionogenic emulsifiers, fatty amines, amphoteric emulsifiers, detergent surfactants, thickeners or preservatives which form the basis for many cosmetic preparations or which are present as so-called active agents or excipients in cosmetic end formulations. The structure of the membranes changes in the presence of such substances, which may result in the destruction of the added carrier system during preparation.

Customary membranes are also exposed to the attack of acids and bases. Thus, it is required, for example, that carrier systems containing phospholipids can only be used in the range of the so-called pH optimum of about pH 6.5. Lowering or raising of the pH results in the hydrolysis of the membrane-forming molecules.

Surprisingly, it has now been found that nanodispersions of suitable composition can, in the presence of amphiphilic substances, be incorporated into cosmetic end formulations over a wide pH range in very simple manner while retaining their morphological and physicochemical properties.

Accordingly, this invention relates to the use of a nanodispersion, which comprises (a) a membrane-forming molecule,
(b) a coemulsifier and
(c) a lipophilic component, in cosmetic end formulations, the nanodispersion being obtainable by ($\alpha$) mixing the components (a), (b) and (c) until a homogeneous clear liquid is obtained (so-called nanodispersion prephase), and ($\beta$) adding the liquid obtained in step ($\alpha$) to the water phase of the cosmetic end formulations, wherein steps ($\alpha$) and ($\beta$) are carried out without any additional supply of energy.

Step ($\alpha$) is usually carried out at room temperature, where necessary with heating and under normal pressure conditions. Mixing is carried out using standard stirring apparatus, for example propeller, angled paddle or magnetic agitators, and without using any special mechanical stirring aids.

Components (a), (b) and (c) (=step ($\alpha$)) are mixed in anhydrous medium, i.e. it is not necessary to add any water.

Step ($\beta$) is carried out by adding the liquid obtained in step ($\alpha$), the nanodispersion pre-phase, to the water phase of the cosmetic end formulations. The particular choice of components (a), (b) and (c) results directly in ultrafine, monodisperse nanodispersions. In this case it is possible to forego homogenisation via nozzle, rotor-stator or ultrasound homogenisers, which is usually carried out to convert coarsely disperse or at least heterodisperse systems to fine monodisperse systems. Step ($\beta$) is thus characterised by the absence of high shear or cavitation forces, e.g. using shear velocities below 10000/s and/or essentially laminar flow (Reynolds number below $10^4$).

Step ($\beta$) is usually carried out at room temperature, which is the range of the respective oil/water phase inversion temperature (PIT).

The nanodispersions characterised by the process steps ($\alpha$) and ($\beta$) contain particles having an average diameter of <50 nm, typically of less than 30 nm. The distribution is monodisperse and corresponds to a Gaussian distribution.

According to this invention, it is preferred to use a nanodispersion which contains, (a) as membrane-forming molecules, substances which are suitable for forming so-called bilayers, (b) as coemulsifiers, substances which preferably form O/W structures and, (c) as lipophilic component, a functional lipophilic active agent customarily used in cosmetics.

The nanodispersion prephase preferably contains ethanol as an additional component (d) in an amount of about 3 to about 30% by weight, for example 7.4 to 14.2% by weight; in this case, the amounts of components (a), (b) and (c) specified hereinafter refer to the total weight of the prephase and the cosmetically active agent.

The nanodispersion preferably contains as component (a) a phospholipid, a hydrated or partially hydrated phospholipid, a lysophospholipid, a ceramide, or mixtures of these compounds.

A very particularly preferred phospholipid is that of formula

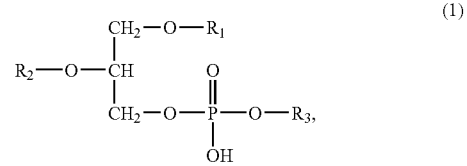

wherein
$R_1$ is $C_{10}$-$C_{20}$acyl;
$R_2$ is hydrogen or $C_{10}$-$C_{20}$acyl $R_3$ is hydrogen, 2-trimethylamino-1-ethyl, 2-amino-1-ethyl; $C_1$-$C_5$alkyl which is unsubstituted or substituted by one or several carboxy, hydroxy or amino groups; the inositol or glyceryl group;

or salts of these compounds.

$C_{10}$-$C_{20}$Acyl is preferably straight-chain $C_{10}$-$C_{20}$alkanoyl containing an even number of carbon atoms and straight-chain $C_{10}$-$C_{20}$alkenoyl containing a double bond and an even number of carbon atoms.

Straight-chain $C_{10}$-$C_{20}$alkanoyl containing an even number of carbon atoms is, for example, n-dodecanoyl, n-tetradecanoyl, n-hexadecanoyl or n-octadecanoyl.

Straight-chain $C_{10}$-$C_{20}$alkenoyl containing a double bond and an even number of carbon atoms is, for example, 6-cis- or 6-trans-, 9-cis- or 9-trans-dodecenoyl, -tetradecenoyl, -hexa-decenoyl, -octadecenoyl or -eicosenoyl, preferably 9-cis-octa-decenoyl (oleoyl), and also 9,12-cis-octadecadienoyl or 9,12,15-cis-octadecatrienoyl.

A phospholipid of formula (1), wherein $R_3$ is 2-trimethylamino-1-ethyl, is referred to by the trivial name lecithin, and a phospholipid of formula (1), wherein $R_3$ is 2-amino-1-ethyl, by the trivial name cephalin. Suitable are, for example, naturally occurring cephalin or lecithin, e.g. cephalin or lecithin from soybeans or chicken eggs with different or identical acyl groups, or mixtures thereof.

The phospholipid of formula (1) may also be of synthetic origin. The expression "synthetic phospholipid" is used to define phospholipids having uniform composition with respect to $R_1$ and $R_2$. Such synthetic phospholipids are preferably the lecithins and cephalins defined above, wherein the acyl groups $R_1$ and $R_2$ have a defined structure and which are derived from a defined fatty acid having a degree of purity greater than about 95%. $R_1$ and $R_2$ may be identical or different and unsaturated or saturated. Preferably, $R_1$ is saturated, for example n-hexadecanoyl, and $R_2$ is unsaturated, for example 9-cis-octadecenoyl (oleoyl). The expression "naturally occurring" phospholipid defines a phospholipid that does not have a uniform composition with respect to $R_1$ and $R_2$. Such natural phospholipids are likewise lecithins and cephalins, wherein the acyl groups $R_1$ and $R_2$ are derived from naturally occurring fatty acid mixtures.

The requirement "substantially pure" phospholipid of formula (1) defines a degree of purity of more than 90% by weight, preferably of more than 95% by weight of the phospholipid of formula (1), which can be demonstrated by means of suitable determination methods, for example by paper chromatography, thin-layer chromatography, by HPLC or by means of enzymatic colour testing.

In a phospholipid of formula (1), $R_3$ defined as $C_1$-$C_4$alkyl is, for example, methyl or ethyl. Methyl is preferred.

$R_3$ defined as $C_1$-$C_5$alkyl substituted by one or several carboxy, hydroxy or amino groups is, for example, 2-hydroxyethyl, 2,3-dihydroxy-n-propyl, carboxymethyl, 1- or 2-carboxyethyl, dicarboxymethyl, 2-carboxy-2-hydroxy-ethyl or 3-carboxy-2,3-dihydroxy-n-propyl, 3-amino-3-carboxy-n-propyl or 2-amino-2-carboxy-n-propyl, preferably 2-amino-2-carboxyethyl.

Phospholipids of formula (1) containing these groups can be present in salt form, for example as sodium or potassium salt.

Phospholipids of formula (1), wherein $R_3$ is the inositol or glyceryl group, are known by the names phosphatidylinositol and phosphatidylglycerol.

The acyl radicals in the phospholipids of formula (1) are also customarily known by the names given in brackets: 9-cis-dodecenoyl (lauroleoyl), 9-cis-tetradecenoyl (myristoleoyl), 9-cis-hexadecenoyl (palmitoleoyl), 6-cis-octadecenoyl (petroseloyl), 6-trans-octadecenoyl (petroselaidoyl), 9-cis-octa-decenoyl (oleoyl), 9-trans-octadecenoyl (elaidoyl), 9,12-cis-octadecadienoyl (linoleoyl), 9,12,15-cis-octadecatrienoyl (linolenoyl), 11-cis-octadecenoyl (vaccenoyl), 9-cis-eicosenoyl (gadoleoyl), 5,8,11,14-cis-eicosatetraenoyl (arachidonoyl), n-dodecanoyl (lauroyl), n-tetra-decanoyl (myristoyl), n-hexadecanoyl (palmitoyl), n-octadecanoyl (stearoyl), n-eicosanoyl (arachidoyl), n-docosanoyl (behenoyl), n-tetracosanoyl (lignoceroyl).

A salt of the phospholipid of formula (1) is preferably cosmetically acceptable. Salts are defined by the existence of salt-forming groups in the substituent $R_3$ and by the free hydroxyl group at the phosphorus atom. The formation of internal salts is also possible. Alkali metal salts, especially the sodium salt, are preferred.

In a particularly preferred embodiment of this invention, purified lecithin from soybeans of the quality LIPOID S 100 or S 75, or a lecithin defined in the monograph USP23/NF 18, is used. Component (a) is preferably used in a concentration of about 0.1 to 30% by weight, such as 2 to 20% by weight, especially 5 to 20% by weight, for example 5.0 to 17.3% by weight, based on the total weight of the components (a), (b) and (c).

Component (b) is preferably an emulsifier or emulsifier mixtures forming the preferred O/W structures.

Especially preferred emulsifiers are
  alkali, ammonium and amine salts of fatty acids. Examples of such salts are the lithium, sodium, potassium, ammonium, triethylamine, ethanolamine, diethanolamine or triethanolamine salts. It is preferred to use the sodium, potassium or ammonium (NR1R2R3) salts, wherein $R_1$, $R_1$ and $R_1$ are each independently of one another hydrogen, $C_1$-$C_4$alkyl or $C_1$-$C_4$hydroxyalkyl.
  saturated and unsaturated alkyl sulfates, such as sodium docecylsulfate and alkane-sulfonates such as sodium dodecanesulfonate;
  salts of colic acid, such as sodium cholate, sodium glycocholate and sodium taurocholate;
  invert soaps (quats), such as zetylpyridinium chloride;
  partial fatty acid esters of sorbitan, such as sorbitan monolaurate;
  sugar esters of fatty acids, such as sucrose monolaurate;
  alkylglucosides, such as n-octylglucoside or n-dodecylglucoside;
  alkylmaltosides, such as n-dodecylmaltoside;
  fatty acid partial glycerides, such as lauric acid monoglyceride;
  $C_8$-$C_{18}$betaines, $C_8$-$C_{24}$alkylamido-$C_1$-$C_4$alkylenebetaines and $C_8$-$C_{18}$sulfobetaines;
  proteins, such as casein;
  polyglycerol esters of fatty acids;
  propylene glycol esters of fatty acids;
  lactates of fatty acids, such as sodium stearoyllactyl-2-lactate;
  fatty alcohol phosphorates.

Emulsifiers of the polyoxyethylene type are very particularly preferred. Examples of such emulsifiers are:
  polyethoxylated sorbitan fatty acid esters, such as polysorbate 80;
  polyethoxylated fatty alcohols, such as oleth-20;
  polyethoxylated fatty acids, such as polyoxyl 20 stearate;
  polyethoxylated vitamin E derivatives, such as vitamin E polyethylene glycol 1000 succinate;
  polyethoxylated lanoline and lanoline derivatives, such as laneth-20;
  polyethoxylated fatty acid glycerides or, especially, partial glycerides, such as polyethoxylated castor oil or diethylene glycol monostearate;
  polyethoxylated alkylphenols, such as ethylphenolpoly (ethylene glycol ether)11;
  sulfuric acid semiester polyethoxylated fatty alcohols and their salts, such as $C_{12}$-$C_{14}$-fatty alcohol ether sulfate-2 EO-sodium salt;
  polyethoxylated fatty amines and fatty acid amides;
  polyethoxylated carbon hydrates
    block polymers of ethylene oxide and propylene oxide, such as poloxamer 188.

The nanodispersion preferably contains as component (b) at least one emulsifier of the polyoxyethylene type, and very particularly preferably an emulsifier of the polyoxyethylene type, or a mixture of these substances.

Component (b) is present in the nanodispersion used according to this invention in a concentration of about 1 to about 50% by weight, such as 15 to about 50% by weight, preferably 15 to 40% by weight, for example 22.7 to 34.0% by weight, based on the total weight of components (a), (b) and (c).

Component (c) is preferably a natural or synthetic or a partially synthetic di- or triglyceride, a mineral oil, silicone oil, wax, fatty alcohol, guerbet alcohol or the ester thereof, a lipophilic functional cosmetic active agent including sunscreens, or a mixture of these substances. Preferred as component (c) is a natural or synthetic or a partially synthetic $C_4$-$C_{18}$triglyceride, or a mixture of a natural or synthetic or a partially synthetic $C_4$-$C_{18}$triglyceride and a lipophilic functional cosmetic active agent.

During preparation of the present nanodispersion, the lipophilic functional cosmetic active agent may be added as part of component (c), i.e. admixed to the oil component, or with the water phase, or both. Addition with the water phase, in total or in part, may be advantageous in case of a lipophilic functional cosmetic active agent, which also exhibits a certain solubility in water (amphiphilic behaviour), as long as the water phase remains a single phase. The weight ratio of lipophilic cosmetically active agent to $C_4$-$C_{18}$triglyceride usually ranges from 1:3 to about 5:1, especially from about 1:1 to 5:1, for example from 1.45:1 to 2.85:1. The lipophilic cosmetically active agent, e.g. of component (c), is particularly preferably a sunscreen or a fat-soluble vitamin.

Even when adding the cosmetically active agent in step (β) with the water phase, the cosmetically active agent benefits from the advantageous carrier effect of the present nanodispersion.

An active agent, active agent composition or active agent extract suitable for skin cosmetics is an ingredient or a mixture of ingredients which is approved for dermal or topic administration.

Examples to be listed are:

active agents which have cleansing action on the skin surface and hair. These include all those substances which are used for cleansing the skin, for example oils, soaps, syndets and solid substances;

active agents having a deodorising and antiperspirant action: these include antiperspirants based on aluminium or zinc salts, deodorants containing bactericidal or bacteriostatic deodorising substances, for example triclosan, hexachlorophene, alcohols and cationic substances, for example quaternary ammonium salts and smell absorbers, for example ®Grillocin (combination of zinc rizinoleate and different additives) or triethylcitrates, optionally in combination with an antioxidant, such as butylhydroxytoluene), or ion exchange resins;

active agents offering protection against sunlight (UV filters): suitable active agents are filter substances (sunscreens) which can absorb the UV radiation from sunlight and convert it into heat. Depending on the desired effect, the following sunscreens are preferred: sunscreens which selectively absorb energy-rich, sunburning UV radiation in the range from about 280 to 315 nm (UV-B absorbers) and which transmit the longwave range from about 315 to 400 nm (UV-A range), and sunscreens which only absorb the longwave radiation of the UV-A range from 315 to 400 nm (UV-A absorbers).

Suitable sunscreens are, for example, organic UV absorbers from the class of the p-aminobenzoic acid derivatives, salicylic acid derivatives, benzophenone derivatives, dibenzoylmethane derivatives, diphenylacrylate derivatives, benzofuran derivatives, polymeric UV absorbers containing one or more than one silicium-organic radical, cinnamic acid derivatives, camphor derivatives, trianilino-s-triazine derivatives, phenylbenzimidazolesulfonic acid and the salts thereof, menthylanthranilates, benzotriazole derivatives, and/or an inorganic micropigment selected from the group consisting of $TiO_2$, zinc oxide or mica encapsulated with aluminium oxide or silicium dioxide.

Examples of p-aminobenzoic acid derivative compounds are:

4-aminobenzoic acid (PABA); ethyldihydroxypropyl-PABA of formula

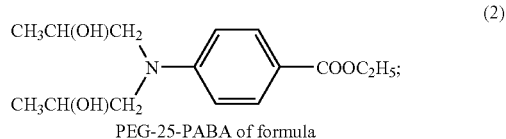

PEG-25-PABA of formula

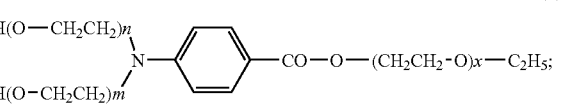

wherein m, n and x have the same meaning and each is at most 25; octyldimethyl PABA of formula

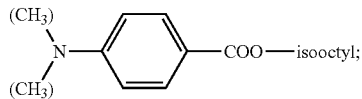  (4)

or glycylaminobenzoate of formula

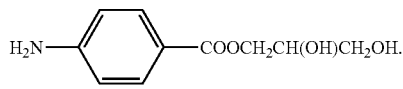  (5)

Example of salicylic acid derivative compounds are:
Homomenthylsalicylate of formula

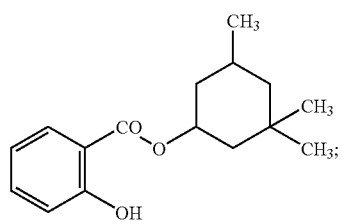  (6)

triethanolaminesalicylate of formula

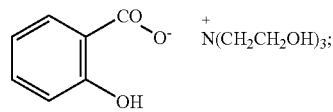  (7)

-continued
amyl-p-dimethylaminobenzoate of formula

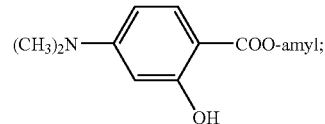  (8)

octylsalicylate of formula

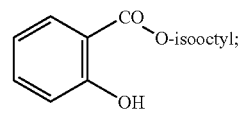  (9)

or 4-isopropylbenzylsalicylate of formula (10)

Examples of benzophenone derivative compounds are:
benzophenone-3-(2-hydroxy-4-methoxybenzophenone), benzophenone-4-(2-hydroxy-4-methoxybenzophenone-5-sulfonic acid) or benzophenone-8-(2,2'-dihydroxy-4-methoxy-benzophenone).

Examples of dibenzoylmethane derivative compounds are:
butylmethoxydibenzoylmethane-[1-(4-tert-butyl)-3-(4-methoxyphenyl)propane-1,3-dione].

Examples of diphenylacrylate derivative compounds are:
octocrylene(2-ethylhexyl-2-cyano-3,3'-diphenylacrylate) or etocrylene(ethyl-2-cyano-3,3'-diphenylacryla Examples of benzofuran derivative compounds are:
3-(benzofuranyl)-2-cyanoacrylate, 2-(2-benzofuranyl)-5-tert-butylbenzoxazole or 2-(p-aminophenyl)benzofuran and, in particular, the compound of formula

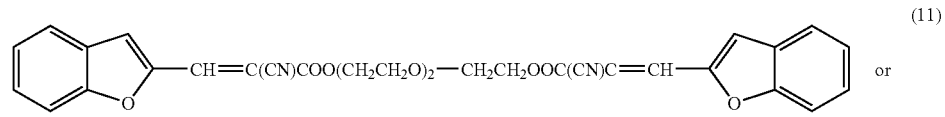  (11)

or

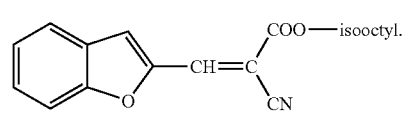  (12)

Examples of polymeric UV absorber compounds containing one or more than one silicium-organic radical are:

benzylidenemalonate derivatives, in particular the compound of formula

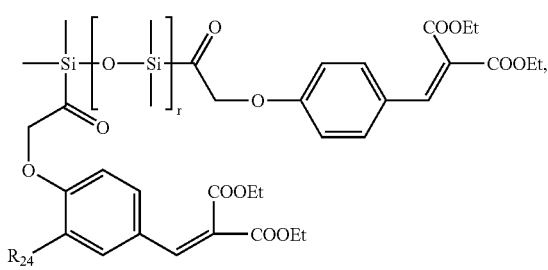
(13)

wherein $R_{24}$ is hydrogen or O-Me, and r is approximately 7; the compound of formula

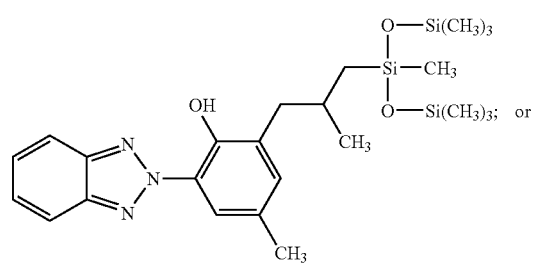
(14)

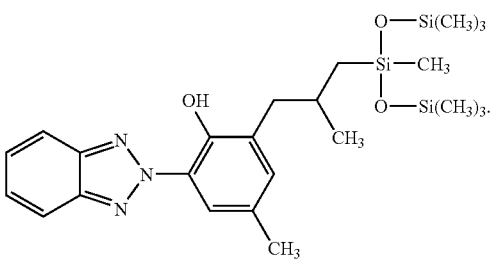
(15)

Examples of cinnamate compounds are:

octylmethoxycinnamate (4-methoxycinnamic acid-2-ethylhexyl ester), diethanolamine-methoxycinnamate (diethanolamine salt of 4-methoxycinnamic acid), isoamyl-p-methoxy-cinnamate (4-ethoxycinnamic acid-2-isoamyl ester), 2,5-diisopropylmethylcinnamate or a cinnamic acid amido derivative.

Examples of camphor derivative compounds are:

4-methylbenzylidene camphor [3-(4'-methyl)benzylidenebornan-2-one], 3-benzylidene-camphor (3-benzylidenebornan-2-one), polyacrylamidomethylbenzylidenecamphor {N-[2(and 4)-2-oxyborn-3-ylidenemethyl)benzyl]acrylamide polymer}, trimoniumbenzylidene-camphorsulfate-[3-(4'-trimethylammonium) benzylidenebornan-2-onemethylsulfate], terephthalydenedicamphorsulfonic acid (3,3'-(1,4-phenylenedimethine)-bis-(7,7-dimethyl-2-oxobicyclo-[2.2.1]heptane-1-methanesulifonic acid}or the salts thereof, or benzylidene-camphorsulfonic acid [3-(4'-sulfo)benzylidenebornan-2-one] or the salts thereof.

Examples of trianilino-s-triazine derivative compounds are:

octyltriazine-[2,4,6-trianilino-(p-carbo-2'-ethyl-1'-oxy)-1,3, 5-triazine and the trianilino-s-triazine derivatives described in U.S. Pat. No. 5,332,568, U.S. Pat. No. 5,252,323, WO 93/17002 and WO 97/03642 and EP-A-0,517,104; the resorcinyltriazines described in EP-A-0,775,698, in particular the compounds of formula

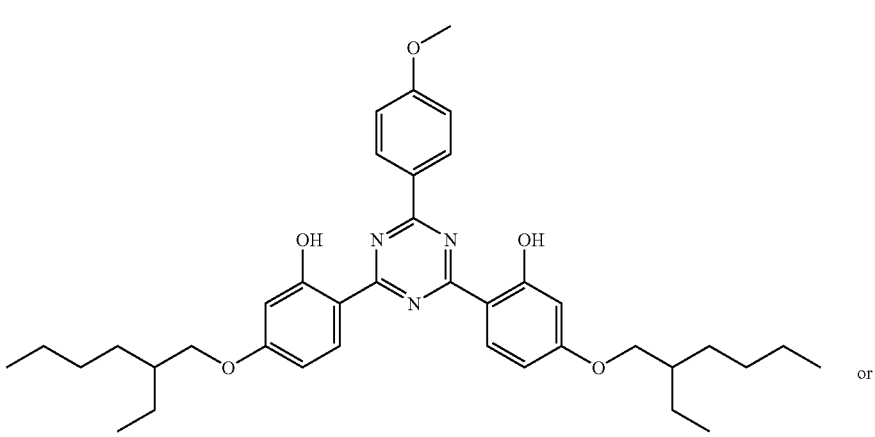
(16)

or

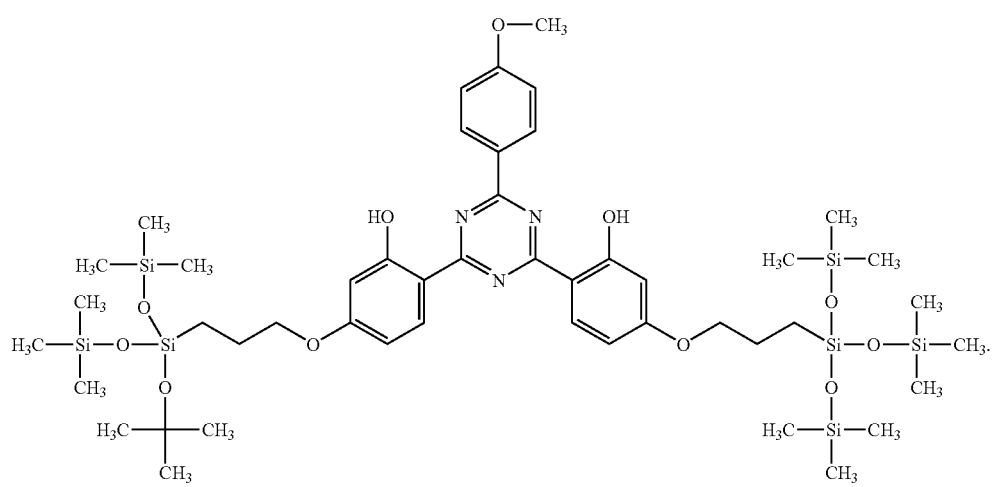

(17)

Examples of benzotriazole compounds are:
2-(2-hydroxy-5-methylphenyl)benzotriazole;
the benzotriazole compounds disclosed in EP-A-0,746, 305, in particular the compound of formula (18)

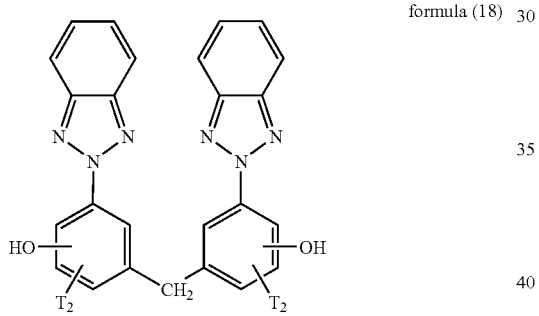

wherein $T_2$ is hydrogen; or $C_1$-$C_8$alkyl;
- insect repellents: repellents are compositions which should prevent insects from touching the skin and getting active there. They repel the insects and slowly evaporate. The most frequently used repellent is dethyltoluamide (DEET). Other customary repellents are to be found in "W. Raab and U. Kindl, "Pflegekosmetik", Gustav-Fischer-Verlag Stuttgart/New York, 1991, p.161;
- active agents protecting against chemical and mechanical attack: these include all those substances which form a barrier between the skin and the outer noxa, such as paraffin oils, silicone oils, vegetable oils, PCL products and lanoline as protection against aqueous solutions, film formers, such as sodium alginate, triethanolamine alginate, polyacrylates, polyvinyl alcohol or cellulose ethers against the action of organic solvents, or substances based on mineral oils, vegetable oils or silicone oils as "lubricants" against high mechanical stresses of the skin;
- moisturising substances: the following substances are used as moisturisers: sodium lactate, urea, alcohols, sorbitol, glycerol, propylene glycol, collagen, elastin or hyaluronic acid;
- active agents having ceratoplastic activity: benzoylperoxide, retinic acid, colloidal sulfur and resorcinol;
- antimicrobial agents, for example triclosan or quaternary ammonium compounds;
- dermally applicable oily or oil-soluble vitamins or vitamin derivatives: e.g. vitamin A (getinol in the form of the free acid or its derivatives), panthenol, pantothenic acid, folic acid, and combinations thereof, vitamin E (tocopherol), F; essential fatty acids; or niacinamide (nicotinic acid amide);
- vitamin-based placenta extracts: active agent compositions mainly with vitamin A, C, E, $B_{21}$ $B_{12}$, folic acid and biotin, amino acids and enzymes and also compounds of the trace elements magnesium, silicium, phosphorus, calcium, manganese, iron or copper.
- skin repair complexes: obtainable from inactivated and desintegrated cultures of bacteria of the bifidus group;
- plants and plant extracts: for example arnica, aloe, beard lichen, ivy, nettle, ginseng, henna, camomile, calendula, rosemary, sage, equisetum or thyme;
- animal extracts: for example royal jelly, propolis, proteins or thymus extracts;
- dermally applicable cosmetic oils: neutral oils of the miglyol 812 type, apricot kernel oil, avocado oil, babassu oil, cottonseed oil, borage oil, thistle oil, groundnut oil, gammaoryzanol, rosehip seed oil, hemp oil, hazelnut oil, currant seed oil, jojoba oil, cherrystone oil, salmon oil, linseed oil, corn oil, macadamia nut oil, almond oil, evening primrose oil, mink oil, olive oil, pecan nut oil, peach kernel oil, pistachio nut oil, rapeseed oil, rice germ oil, castor oil, safflower oil, sesame oil, soybean oil, sunflower oil, tea tree oil, grapeseed oil or wheat germ oil.

Component (c) is present in the nanodispersions used according to this invention in a concentration of preferably 0.1 to 80% by weight; the total amount of triglyceride in component (c) and the cosmetically active agent in the present nanodispersion preferably ranges from 20 to 70%, especially 30 to 70% by weight, for example about 50% by weight such as 47.6 to 56.3% by weight of total prephase and active agent, such as the total weight of components (a), (b) and (c).

Components (a), (b) and (c) can be present in the nanodispersions used according to this invention as individual compounds or as mixtures of several different individual components. At least one component (a), (b) or (c) in the nanodispersion composition is usually a functional active agent used in cosmetics for treating or protecting the skin, mucosae and hair.

The nanodispersion used according to this invention optionally comprises as facultative component (d) a solubilising agent, preferably a $C_2$-C8alcohol, such as ethanol or propylene glycol.

A nanodispersion containing the components (a), (b), (c) and optionally (d) is distinguished by favourable phase properties of the solubilised functional cosmetic agent. Thus if there is opalescence and transparency in incident light, only a very slight turbidity shows that the dispersion is physically still different from the ideal state of a genuine molecular solution. Electron microscopic images show that a population of more than 98% is present in a Gaussian distribution as a suspension of particles (nanoparticles) having a particle size of less than about 50 nm, typically of less than about 30 nm; at least 90% of the particles then usually have a size from the range 1 to 30 nm (number average). However, these distinctions from a genuine solution can be tolerated because of the particularly good homogeneity properties of the dispersion which can be evidenced, for example, by a surprisingly high storage stability, e.g. no separation after storing for several months at temperatures of up to room temperature (stability to be expected by extrapolation: more than two years). Laser light scattering measurements and electron microscopic analysis (Cryo-TEM) confirm the very small size and excellent homogeneity of the nanoparticles present in the nano-dispersion.

Another advantage of the nanodispersions used according to this invention is that they are easy to prepare.

The nanodispersions characterised by claim 1 are used according to this invention for cosmetic end formulations.

This invention also relates to the so-called nanodispersion prephase characterised in step (α), which is obtainable by mixing the components (a) membrane-forming molecules,
(b) coemulsifier,
(c) lipophilic component and, optionally,
(d) a $C_2$-$C_8$alcohol, preferably propylene glycol and, more preferably, ethanol until a homogeneous clear liquid is obtained, mixing being carried out in anhydrous medium. These nanodispersion prephases can likewise be directly used in accordance with this invention for cosmetic end formulations.

Cosmetic end formulations include a very wide range of cosmetic products. Suitable products are, for example, especially the following:

skin-care products, for example skin washing and cleansing products in the form of bars of soap or liquid soaps, syndets or washing pastes, bath products, for example liquid (foam baths, milks, shower products) or solid bath products, such as bath pearls and bath salts;

skin-care products, such as skin emulsions, multiple emulsions or skin oils;

decorative body-care products, for example face make-ups in the form of day or powder creams, face powders (lose and compressed), rouge or cream make-ups, eye-care products, for example eye shadow products, mascara, eyeliners, eye creams or eye-fix creams; lip-care products, for example lipstick, lip gloss, lip liner, nail-care products, such as nail varnish, nail varnish remover, nail hardeners or cuticle removers;

feminine hygiene products, such as feminine hygiene washing lotions or sprays;

foot-care products, for example foot baths, foot powders, food creams or foot balms, special deodorants and antiperspirants or products for scrubbing off callouses;

sunscreens, such as sun milks, lotions, creams, oils, sunblockers or tropicals, pre-sun products or after-sun products;

suntanning products, for example self-tanning creams;

depigmenting products, for example products for bleaching or lightening skin;

insect repellents, for example insect oils, lotions, sprays or sticks;

deodorants, for example deodorant sprays, non-aerosol sprays, deodorant gels, sticks or roll-ons;

antiperspirants, for example antiperspirant sticks, creams or roll-ons;

products for cleansing and treating impure skin, for example syndets (solid or liquid), peeling or scrubbing products or peeling masks;

chemical depilatory products, for example depilatory powders, liquid depilatory products, creamy or pasty depilatory products, depilatory gels or aerosol foams;

shaving products, for example shaving soap, foaming shaving creams, non-foaming shaving creams, shaving foams and gels, preshaving products for dry shaving, aftershaves or aftershave lotions;

scents, for example perfumes (Eau de Cologne, Eau de Toilette, Eau de Parfum, Parfum de Toilette, perfume), perfume oils or perfume creams;

products for oral and dental hygiene as well as for dentures, for example toothpastes, tooth gels, tooth powders, mouth-wash concentrates, anti-plaque mouth-washes, denture cleaning products or denture adhesion products;

cosmetic formulations for hair treatment, for example hair washes in the form of shampoos, hair conditioners, hair-care products, for example pretreatment products, hair tonics, hair styling creams and gels, pomades, hair rinses, deep conditioning treatments, intensive hair care treatments, hair setting products, for example waving agents for perms (hot wave, mild wave, cold wave), hair straightening products, liquid hair fixatives, hair foams, hair sprays, bleaching agents, for example hydrogen peroxide solutions, bleaching shampoos, bleaching creams, bleaching powders, bleaching pastes or oils, temporary, semitemporary or permanent hair dyes, products containing self-oxidising dyes, or natural hair dyes, such as henna or camomile.

The end formulations listed above can be in a very wide range of forms of presentation, for example in the form of liquid formulations as an O/W emulsion, in the form of a gel, in the form of an oil, cream, milk or lotion, in the form of a powder, lacquer, pellets or make-up, in the form of a stick, in the form of a spray (spray with propellant or non-aerosol spray) or an aerosol, in the form of a foam, or in the form of a paste.

The liquid and semisolid forms of presentation in this case contain the nanodispersion with the components (a), (b) and (c) in the aqueous phase, and one or several of the above functional cosmetic active agent(s). Solid forms of presentation contain the nanodispersion in the dehydrated form, the dehydration of the nanodispersion usually being carried out by freeze-drying or spray-drying in the presence of customary auxiliaries. For some end formulations it is advantageous to replace the nanodispersion with the corresponding nanodispersions prephase.

Emulsions are heterogeneous systems consisting of two liquids (phases) which are not, or only partly, miscible with each other. One phase is present in the form of droplets (dispersed or inner phase), whereas the other forms a continuous phase as a liquid. In the case of an O/W emulsion, which is basically characterised by water, oil droplets are finely dispersed in water.

Creams are usually spreadable in the temperature range from room to skin temperature, whereas lotions or milks tend to be pourable.

Gels are semisolid, more or less transparent systems in which the so-called gel former forms a three-dimensional network in which a liquid is immobilised. The clear to opaque hydrogels consist primarily of water, water-soluble substances and thickeners or gel formers. If lipids are additionally incorporated, the slightly creamy-looking hydrodispersion gels are obtained. In contrast, the oleogels are free of water and contain lipids as liquid components.

The cosmetic end formulation containing one or several of the above ingredients which may be in the form of the above-mentioned forms of presentation, contains the nanodispersion used according to this invention preferably in a concentration of 0.01 to 100, preferably of 0.01 to 20.0, more preferably of 0.05 to 5% by weight.

These end formulations are another subject matter of this invention.

The end formulations in this case contain the nanodispersion in their aqueous phase in a concentration of 0.01 to 20.0, preferably of 0.05 to 10 and, more preferably of 0.1 to 5% by weight.

The end formulation used according to this invention can also contain other components, for example emollients, emulsion stabilisers, skin moisturisers, suntanning accelerators, thickeners, such as xanthane, moisture retention agents, such as glycerol, preservatives, such as parabene, antioxidants, as well as fragrances and colourants.

The basic formulations for the cosmetic end formulations according to Examples 14 to 21 are prepared in accordance with the instructions in "Kosmetik; Entwicklung, Herstellung und Anwendung kosmetischer Mittel" (Ed.: W. Umbach, Georg Thieme Verlag Stuttgart, New York) and with the documentations from "DGK Fortbildungskurs 1998, Entwicklung moderner Hautpflegemittel".

The end formulations are prepared by the customary known methods, some of which are described in the above literature. In the case of liquid and semisolid end formulations, the nanodispersions are always incorporated into the aqueous phase of the end formulations. To this purpose, they are taken up in a small proportion of the aqueous phase and are added, as active agent phase, as last phase during the preparation of a formulation at about 20 to 30° C. It is also possible to add instead of the nanodispersion the corresponding nanodispersion prephase to the water phase of the end formulation. He nanodispersion prephase is added to the water phase with stirring and preferably at a temperature in the range of the respective oil/water phase inversion temperature (PIT).

In the case of solid end formulations it is advantageous to admix the dehydrated form of the nanodispersion to the solid substance mixture.

The cosmetic end formulation is preferably used for the treatment and protection of skin, mucosae or hair and, very particularly, as sunscreen or as an after-sun preparation.

The nanodispersions used according to this invention can also be used as transport vehicles for oil-soluble dyes.

In another of its aspects, this invention thus relates to the use of the nanodispersion defined in claim 1 as carrier system for oil-soluble dyes.

Suitable dyes are of synthetic or also of natural origin and are composed from all known chromophores, for example azo, azoic, anthraquinone, caratenoid, quinoline, xanthene, diarylmethane, triarylmethane, stilbene, indigoid, phtalocyanine, nitro dyes as well as all other known chromophores, such as are also listed in Colour Index under Cl 11000 to Cl 77999.

Of these dyes, those are particularly interesting which are at least partially soluble in organic media such as oils. This includes, for example, those dyes which are called solvent dyes or disperse dyes, the disperse dyes also including the group of the unloaded, directly absorbing hair dyes, for example derivatives of nitrobenzene or of nitrodiphenylamine.

Examples of solvent dyes which may be used in accordance with this invention are: Solvent Black 3 (Cas-No.: 4197-25-5); Solvent Black 5 (Cas-No.: 11099-03-9); Solvent Blue 35 (Cas-No.: 12769-17-4); Solvent Green 3; Solvent Green 7 (Cas-No.: 6358-69-6); Solvent Orange 1 (Cas-No.: 2051-85-6); Solvent Red 24 (Cas-No.: 85-83-6); Solvent Red 43 (Cas-No.: 15086-94-9); Solvent Red 48 (Cas-No.: 13473-26-2); Solvent Red 49:1 (Cas-No.: 6373-07-5); Solvent Red 72 (Cas-No.: 596-03-2); Solvent Yellow 44 (CAS No.: 2478-20-8); Solvent Yellow 18 (CAS No.: 6407-76-9).

Examples of disperse dyes which may be used in accordance with this invention are: Disperse Black 9 (CAS No.: 12222-60-4); Disperse Blue 1 (CAS Nos.: 2475-45-8); Disperse Blue 3 (CAS No.: 2475-46-9); Disperse Brown 1 (CAS No.: 23355-64-8); Disperse Orange 3 (CAS No.: 730-40-5); the compound of formula

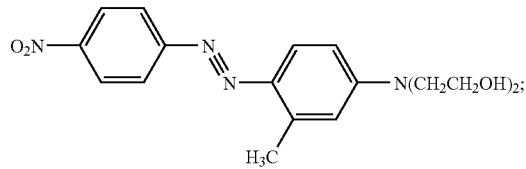

Disperse Violet 1 (CAS-No.: 128-95-0); Disperse

Violet 4 (CAS-No.: 1220-94-6); the compound of formula

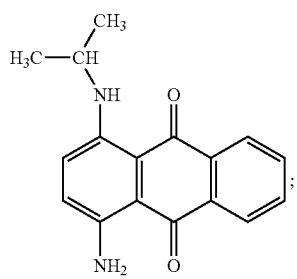

examples of (unloaded) directly absorbing hair dyes are:

HC Blue No. 2 (CAS-No.: 33229-34-4); HC Blue No. 4 (reaction product of N-methyl-1,4-diaminoanthraquinon epichlorohydrin and monoethanolamine); HC Blue No. 5 (CAS-No.: 68478-64-8); the compound of formula

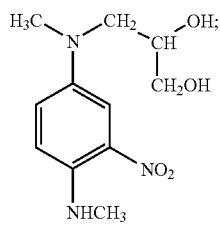

HC Blue No. 7 (Cas-No.: 90817-34-8); HC Blue No. 8(Cas-No.: 22366-99-0); HC Blue No. 9 (Cas-No.: 114087-42-2); HC Blue No. 10 (Cas-No.: 102767-27-1); HC Blue No. 11 (Cas-No.: 23920-15-2); HC Blue No. 12 (Cas-No.: 132885-85-9); the compound of formula

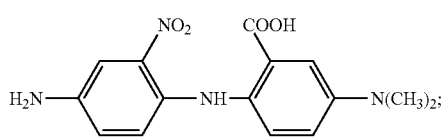

HC Blue No. 14 (Cas-No.: 99788-75-7); HC Orange No. 1 (Cas-No.: 54381-08-7);, HC Orange No. 2 (Cas-No.: 85765-48-6), HC Orange No. 3 (Cas-No.: 81612-54-6); the compound of formula

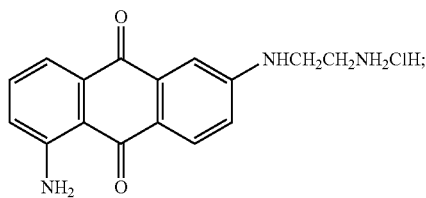

HC
Red No. 1 (Cas-No.: 2784-89-6); HC Red No. 3 (Cas-No.: 2871-01-4); HC Red No. 7 (Cas-No.: 24905-87-1); HC Red No. 8 (Cas-No.: 13556-29-1); HC Red No. 9 (Cas-No.: 56330-88-2); HC Red No. 10 (Cas-No.: 95576-89-9);, HC Red No. 11 (Cas-No.: 95576-92-4), HC Red
No.13 (Cas-No.: 94158-13-1); the compound of formula

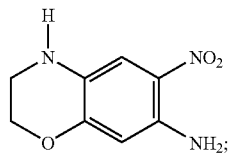

HC Violet No. 1
(Cas-No.: 82576-75-8); the compound of formula

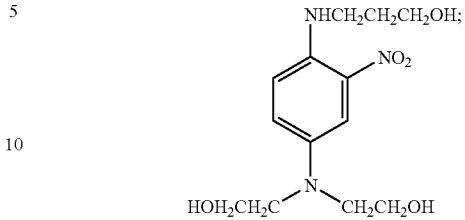

HC Yellow No.
2 (Cas-No.: 4926-55-0); HC Yellow No. 4 (Cas-No.: 59820-43-8); HC Yellow No. 5 (Cas-No 56932-44-6); HC Yellow No. 6 (Cas-No.: 104335-00-6); the compound of formula

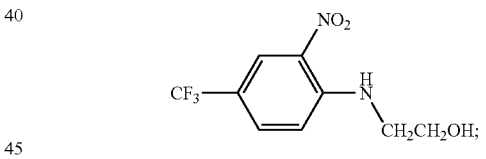

HC Yellow No. 8 (Cas-No.: 66612-11-1);
HC Yellow No. 9 (Cas-No.: 86419-69-4); HC Yellow No. 10 (Cas-No.: 109023-83-8);
HC Yellow No. 11 (Cas-no.: 73388-54-2); HC Yellow No. 12 (Cas-No.: 59320-13-7);
HC Yellow No. 13 (Cas-No.: 10442-83-8); the compound of formula

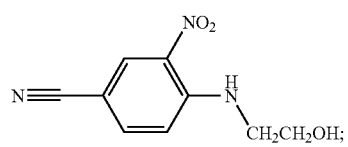

HC compound of formula

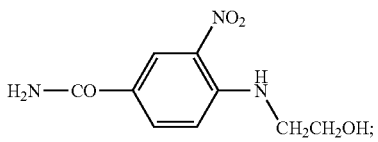

the compound of formula

HC Brown No. 1 (Cas-No.: 83803-98-9); HC Brown No. 2 (Cas-No.: 83803-99-0); HC Green No. 1 (Cas-No.: 52136-25-1).

The nanodispersions used according to this invention can have the following functions:
- being carriers for allowing dyes to penetrate through certain potential walls into media such as skin, hair or nails;
- protecting the dyes from other ingredients of a formulation (or vice versa, protecting the formulation from another dyes), for example in order to eliminate incompatibilities between formulation and solid. The dye is then separated in the core of the nanodispersion from the remainder of the formulation. Thus it is possible to prevent chain reactions with other ingredients which reactions are photo-initiated by the dye;
- introducing dyes which are only soluble in oil phases into aqueous systems and stabilising them. The dye is then dissolved in the core of the nanodispersion (oil phase) and the nanodispersion particle is in turn dispersed in the aqueous phase.

In the following Examples, percentages are by weight. Unless otherwise stated, amounts of compounds used are based on the pure substance.

Working Examples for nanodispersion prephases

EXAMPLE 1

Miglyol 812 Nanodispersion Prephase

| soybean lecithin | 17.30% |
| polysorbate 80 | 34.00% |
| miglyol 812 | 34.50% |
| ethanol | 14.20% |

Preparation: Miglyol 812 and polysorbate 80 are mixed. The soybean lecithin is dissolved in ethanol and added to this mixture, resulting in a homogeneous clear liquid.

EXAMPLE 2

Miglyol 812 Nanodispersion Prephase

| soybean lecithin | 17.30% |
| oleth-20 | 34.00% |
| miglyol 812 | 34.50% |
| ethanol | 14.20% |

Preparation: Miglyol 812 and oleth-20 are mixed, with heating. The soybean lecithin is dissolved in ethanol and added to this mixture, resulting in a homogeneous clear liquid.

EXAMPLE 3

Miglyol 812 Nanodispersion Prephase

| soybean lecithin | 17.30% |
| laneth-20 | 34.00% |
| miglyol 812 | 34.50% |
| ethanol | 14.20% |

Preparation: Miglyol 812 and Laneth-20 are mixed, with heating. The soybean lecithin is dissolved in ethanol and added to this mixture, resulting in a homogeneous clear liquid.

EXAMPLE 4

Miglyol 812 Nanodispersion Prephase

| soybean lecithin | 17.30% |
| vitamin E polyethylene glycol succinate (vitamin E TPGS, Eastman) | 34.00% |
| miglyol 812 | 34.50% |
| ethanol | 14.20% |

Preparation: Miglyol 812 and vitamin E polyethylene glycol succinates are mixed, with heating. The soybean lecithin is dissolved in ethanol and added to this mixture, resulting in a homogeneous clear liquid.

EXAMPLE 5

Vitamin E Acetate Nanodispersion Prephase

| soybean lecithin | 9.00% |
| polysorbate 80 | 34.00% |
| vitamin E acetate | 36.60% |
| miglyol 812 | 13.00% |
| ethanol | 7.40% |

Preparation: Miglyol 812, vitamin E acetate and polysorbate 80 are mixed. The soybean lecithin is dissolved in ethanol and added to this mixture, resulting in a homogeneous clear liquid.

EXAMPLE 6

Parsol MCX/Parsol 5000 Nanodispersion Prephase

| soybean lecithin | 5.00% |
| polysorbate 80 | 34.00% |
| parsol MCX (octyl methoxycinnamate) | 25.90% |
| parsol 5000 (4-methylbenzylidene camphor) | 11.10% |
| miglyol 812 | 13.00% |
| ethanol | 11.00% |

Preparation: Parsol 5000 is dissolved in Parsol MXC and mixed with miglyol 812 and polysorbate 80. The soybean lecithin is dissolved in ethanol and added to this mixture, resulting in a homogeneous clear liquid.

Working Examples for Nanodispersions

EXAMPLE 7

Miglyol 812 Nanodispersion

| | |
|---|---|
| soybean lecithin | 1.73% |
| polysorbate 80 | 3.40% |
| miglyol 812 | 3.45% |
| ethanol | 1.42% |
| aqua purificata | ad 100.00% |

Preparation: The water phase (e.g. 90 kg) is placed, with stirring (e.g. magnetic agitator), in a vessel at 50° C. The liquid nanodispersion prephase of Example 1 (e.g. 10 kg) is added to the water phase with stirring (e.g. using a magnetic agitator).

EXAMPLE 8

Miglyol 812 Nanodispersion

| | |
|---|---|
| soybean lecithin | 1.73% |
| oleth-20 | 3.40% |
| miglyol 812 | 3.45% |
| ethanol | 1.42% |
| aqua purificata | ad 100.00% |

The preparation is carried out in analogy to the procedure of Example 7.

EXAMPLE 9

Migylol 812 Nanodispersion

| | |
|---|---|
| soybean lecithin | 1.73% |
| laneth-20 | 3.40% |
| miglyol 812 | 3.45% |
| ethanol | 1.42% |
| aqua purificata | ad 100.00% |

The nanodispersion is prepared in analogy to the procedure of Example 7.

EXAMPLE 10

Miglyol 812 Nanodispersion

| | |
|---|---|
| soybean lecithin | 1.73% |
| vitamin E polyethylene glycol succinate (vitamin E TPGS, Eastman) | 3.40% |
| miglyol 812 | 3.45% |
| ethanol | 1.42% |
| aqua purificata | ad 100.00% |

The nanodispersion is prepared in analogy to the procedure of Example 7.

EXAMPLE 11

Dexpanthenol Nanodispersion

| | |
|---|---|
| dexpanthenol | 5.00% |
| soybean lecithin | 1.73% |
| polysorbate 80 | 3.40% |
| miglyol 812 | 3.45% |
| ethanol | 1.42% |
| aqua purificata | ad 100.00% |

Preparation: The water phase containing dexpanthenol (e.g. 90 kg) is placed, with stirring (e.g. magnetic agitator), at 50° C. in a vessel. The liquid nanodispersion prephase of Example 1 (e.g. 10 kg) is added to the water phase with stirring (e.g. by means of a magnetic agitator).

EXAMPLE 12

Vitamin E Acetate Nanodispersion

| | |
|---|---|
| vitamin E acetate | 2.00% |
| soybean lecithin | 0.49% |
| polysorbate 80 | 1.86% |
| miglyol 812 | 0.71% |
| ethanol | 0.63% |
| aqua purificata | ad 100.00% |

Preparation: The water phase (e.g. 94.54 kg) is placed, with stirring (e.g. magnetic agitator), at 50° C. in a vessel. The liquid nanodispersion prephase of Example 5 (e.g. 5.46 kg) is added to the water phase with stirring (e.g. by means of a magnetic agitator).

EXAMPLE 13

Parsol MCX/Parsol 5000 Nanodispersion

| | |
|---|---|
| parsol MCX (octyl methoxycinnamate) | 2.59% |
| Parsol 5000 (4-methylbenzylidene camphor) | 1.11% |
| miglyol 812 | 1.30% |
| soybean lecithin | 0.50% |
| polysorbate 80 | 3.40% |
| ethanol | 1.10% |
| aqua purificata | ad 100.00% |

The nanodispersion is prepared in analogy to the procedure or Example 7. Particle sizes and particles size distribution are compiled in the following Table.

TABLE 1

| Nanodispersion | Particle diameter[1] [nm] | Standard deviation [nm] | Particle size distribution |
|---|---|---|---|
| migylol 812 nanodispersion Example 7 | 13.8 | 4.1 | Gauss |
| dexpanthenol nanodispersion Example 11 | 19.7 | 5.4 | Gauss |

TABLE 1-continued

| Nanodispersion | Particle diameter[1] [nm] | Standard deviation [nm] | Particle size distribution |
|---|---|---|---|
| vitamin E acetate nanodispersion Example 12 | 12.2 | 5.5 | Gauss |
| parsol MCX/parsol 5000 nanodispersion Example 13 | 14.6 | 5.2 | Gauss |

[1]The particle size diameters and particle size distributions are determined via laser light scattering (Nicomp 370 Submicron Particle Sizer, number weighting).

Dexpanthenol Nanodispersion (Example 11)

TABLE 2

| Storage conditions | | | | Standard | |
|---|---|---|---|---|---|
| Duration [months] | Temperature [° C.] | pH | Diameter[2] [nm] | deviation [nm] | Dexpanthenol[3] content [%] |
| 0 | | 6.1 | 19.7 | 5.4 | 5.37 |
| 3 | 7 | 6.1 | 19.0 | 6.7 | 5.36 |
|  | 25 | 6.1 | 22.2 | 7.7 | 5.32 |
|  | 40 | 6.3 | 36.6 | 14.2 | 5.23 |
| 6 | 7 | 6.1 | 20.8 | 7.3 | 5.30 |
|  | 25 | 6.2 | 24.1 | 9.2 | 5.26 |
|  | 40 | 6.4 | 35.4 | 17.7 | 5.20 |

[2]The particle diameters and particle size distribution are determined via laser light scattering (Nicomp 370 Submicron Particle Sizer, volume weighting)
[3]The dexpanthenol content is determined via HPLC Vitamin E Acetate Nanodispersion (Example 12)

TABLE 3

| Storage conditions | | | | Standard | Vitamin E |
|---|---|---|---|---|---|
| Duration [months] | Temperature [° C.] | pH | Diameter[4] [nm] | deviation [%] | acetate content [%][5] |
| 0 | | 6.1 | 12.2 | 5.5 | 2.04 |
| 3 | 7 | 6.1 | 16.1 | 6.6 | 2.02 |
|  | 25 | 6.1 | 17.5 | 7.0 | 2.04 |
|  | 40 | 6.0 | 15.4 | 6.8 | 2.01 |
| 6 | 7 | 6.1 | 17.0 | 6.9 | 2.04 |
|  | 25 | 6.0 | 17.6 | 7.2 | 2.03 |
|  | 40 | 6.0 | 20.8 | 7.9 | 2.02 |

[4]The particle diameters and particle size distributions are determined via laser light scattering (Nicomp 370 Submicron Particle Sizer, volume weighting)
[5]The vitamin E acetate content is determined via HPLC Working Examples for Cosmetic End Formulations with Nanodispersions

| | |
|---|---|
| polyglycerol methyl glucose distearate | 2.00% |
| capric/capryl triglyceride | 6.50% |
| mineral oil | 6.50% |
| glycerol | 3.00% |
| nanodispersion of Example 12 | 5.00% |
| carbomer | 0.20% |
| alcohol | 10.00% |
| phenoxyethanol + methyl-, ethyl-, propyl-, butylparabene | 0.30% |
| perfume | 0.30% |
| sodium hydroxide (45%) | 0.09% |
| water | ad 100.00% |

EXAMPLE 15

Day Cream with UV Protection (O/W)

| | |
|---|---|
| PEG-5 glycerol stearate | 5.0% |
| steareth-21 | 2.0% |
| mineral oil | 30.0% |
| cetyl alcohol | 2.0% |
| microcrystalline wax | 1.0% |
| propylene glycol | 6.0% |
| nanodispersion of Example 13 | 10.0% |
| phenoxyethanol + methyl-, ethyl-, propyl-, butylparabene | 0.3% |
| water | ad 100.0% |

EXAMPLE 16

Liquid Syndet Having Fat-restoring Properties

| | |
|---|---|
| fatty alcohol ether sulfate | 7.5% |
| fat restoring agent | 3.0% |
| pearl lustre | 2.0% |
| thickener | 1.0% |
| nanodispersion of Example 10 | 5.0% |
| perfume | 0.3% |
| water | ad 100.0% |

EXAMPLE 17

Foam Bath Having Treatment Properties

| | |
|---|---|
| sodium lauryl ether sulfate | 9.0% |
| coconut fatty acid diethanolamide | 2.0% |
| polyglycol fatty acid ester (3EO) | 3.0% |
| perfume | 1.0% |
| nanodispersion of Example 7 | 4.0% |
| preservative, citric acid, sodium chloride, water | ad 100.0% |

EXAMPLE 18

Soothing O/W Lotion

| | |
|---|---|
| stearic acid | 1.50% |
| sorbitan monostearate | 1.00% |
| sorbitan monooleate | 1.00% |
| mineral oil | 7.00% |
| cetyl palmitate | 1.00% |
| polymethylsiloxane | 1.50% |
| glycerol | 2.00% |

-continued

| | |
|---|---|
| 1.2-propylene glycol | 2.00% |
| nanodispersion of Example 11 | 3.00% |
| polyacrylic acid | 0.15% |
| sodium hydroxide | 0.30% |
| perfume | 0.50% |
| preservative, water | ad 100.00% |

EXAMPLE 19

Skin Protecting W/O Lotion

| | |
|---|---|
| glycerol sorbitan fatty acid ester | 2.0% |
| polyethoxy fatty acid ester | 2.0% |
| isopropylisostearate | 5.0% |
| mineral oil | 7.0% |
| isopropylpalmitate | 4.0% |
| wheat germ oil | 3.0% |
| propylene glycol | 3.8% |
| nanodispersion of Example 12 | 5.0% |
| MgSO$_4$ × 7H2O | 0.7% |
| perfume | 0.5% |
| perservative, water | ad 100.0% |

EXAMPLE 20

Make-up Cream

| | |
|---|---|
| glycerol monostearate | 4.0% |
| cetyl alcohol | 1.0% |
| stearic acid | 2.0% |
| mineral oil | 4.5% |
| cetylstearyloctanoate | 5.0% |
| octylpalmitate | 3.0% |
| talcum | 4.0% |
| titanium dioxide | 1.5% |
| iron oxide | 0.8% |
| propylene glycol | 5.0% |
| polyethoxysorbitan monolaurate | 1.0% |
| xanthane | 0.4% |
| magnesium-aluminium-silicate | 0.3% |
| glycerol | 5.0% |
| nanodispersion of Example 13 | 5.0% |
| preservative, water | ad 100.0% |

EXAMPLE 21

Dexpanthenol Controlled Dosage Spray

| | |
|---|---|
| phenoxyethanol | 0.5% |
| nanodispersion of Example 11 | ad 100.0% |

What is claimed is:

1. A method of preparing a cosmetic formulation of a lipophilic cosmetic active agent in the form of an-oil-in-water nanodispersion, which comprises (α) preparing a nanodispersion prephase by mixing (a) 0.1 to 30% by weight of a phospholipid,
(b) 1 to 50% by weight of a polyoxyethylene coemulsifier selected from the group consisting of polyethoxylated fatty alcohols, polyethoxylated fatty acids, polyethoxylated vitamin E derivatives, polyethoxylated lanoline and lanoline derivatives, and polyethoxylated fatty acid glycerides,
(c) a lipophilic component comprising a natural or synthetic or a partially synthetic $C_4$-$C_{18}$triglyceride, and
(d) 3 to 30% by weight of ethanol, until a homogeneous clear liquid is obtained, and
(β) adding the liquid obtained in step (α) to a water phase, where component (c) used in step (α), or the water phase in step (β), or both, additionally contain a lipophilic cosmetically active agent, where the total weight of lipophilic cosmetically active agent and $C_4$-$C_{18}$triglyceride of component (c) ranges from 20 to 70% by weight, and where the percentages relate to sum of the weight of the components (a), (b), (c), (d) and the lipophilic cosmetically active agent, wherein step (β) is carried out in the absence of high shear or cavitation forces.

2. A method according to claim 1, wherein step (α) consists essentially of mixing of
(a) 2 to 20% by weight of the phospholipid,
(b) 15 to 50% by weight of the polyoxyethylene coemulsifier,
(c) the lipophilic component consisting of the $C_4$-$C_{18}$triglyceride and, optionally, the lipophilic cosmetically active agent, and
(d) 3 to 30% by weight of ethanol.

3. A method according to claim 1, wherein the particles in the nanodispersion have an average diameter of less than 50 nm.

4. A method according to claim 3, wherein the average particle diameter obtained is less than 30 nm.

5. A method according to claim 1, wherein essentially no water is added during step (α), which step essentially consists of the mixing of components (a), (b), (c) and (d).

6. A method according to claim 3, wherein step (β) is carried out without homogenisation.

7. A method according to claim 1, wherein the water phase is pure water or water containing a cosmetically active agent or up to 20% by weight of formulation aids and/or salts or both.

8. A method according to claim 1, wherein 1 part by weight of the nanodispersion prephase is added to 5 to 100 parts by weight of the water phase.

9. A method according to claim 2, wherein the total weight of the lipophilic cosmetically active agent is contained in component (c) added in step (α).

10. A method according to claim 1, wherein component (a) is lecithin, and the lipophilic cosmetically active agent is selected from the group consisting of sunscreens and fat-soluble vitamins.

11. A method of preparing a cosmetic formulation of a lipophilic cosmetic active agent in the form of an-oil-in-water nanodispersion, which comprises (α) preparing a nanodispersion prephase by mixing
(a) 2 to 20% by weight of a phospholipid,
(b) 15 to 50% by weight of a polyoxyethylene coemulsifier selected from the group consisting of polyethoxylated sorbitan fatty acid esters, polyethoxylated fatty alcohols, polyethoxylated fatty acids, polyethoxylated vitamin E derivatives, polyethoxylated lanolin and lanolin derivatives, polyethoxylated fatty acid glycerides, polyethoxylated alkylphenols, sulfuric acid semiesters, polyethoxylated fatty alcohols and their salts, polyethoxylated fatty amines and fatty acid amides, and polyethoxylated carbohydrates, (c) a lipophilic component comprising a natural or synthetic or a partially synthetic $C_4$-$C_{18}$triglyceride, and
(d) 3 to 30% by weight of ethanol, until a homogeneous clear liquid is obtained, and
(β) adding the liquid prephase obtained in step (α) to a water phase, where component (c) used in step (α), or the water phase in step (β), or both, additionally contain a lipophilic cosmetically active agent, where the total weight of lipophilic cosmetically active agent and $C_4$-$C_{18}$triglyceride of component (c) ranges from 20 to 70% by weight, and the weight ratio of total lipophilic cosmetically active agent to $C_4$-$C_{18}$triglyceride of component (c) ranges from 1:3 to 5:1, and where percentages relate to sum of the weight of the components (a), (b), (c), (d) and the lipophilic cosmetically active agent, wherein step (β) is carried out in the absence of high shear or cavitation forces.

12. A method according to claim 11, wherein step (α) comprises mixing of
(a) 5 to 20% by weight of the phospholipid,
(b) 15 to 40% by weight of the polyoxyethylene coemulsifier, and
where the total weight of lipophilic cosmetically active agent present in the nanodispersion and $C_4$-$C_{18}$triglyceride of component (c) ranges from 30 to 70% by weight.

13. A method according to claim 11, wherein none of steps (α) or (β) comprises addition of a sphingolipid or glycolipid.

14. A method according to claim 1, wherein component (b) in the nanodispersion is selected from the group consisting of polyethoxylated fatty alcohols, polyethoxylated fatty acids, polyethoxylated vitamin E derivatives, polyethoxylated lanolin and the derivatives thereof, and polyethoxylated fatty acid glycerides.

15. A method according to claim 11 of preparing a cosmetic formulation of a lipophilic cosmetic active agent in the form of an-oil-in-water nanodispersion, which method comprises (α) preparing a nanodispersion prephase by mixing
(a) 5.0 to 17.3% by weight of the phospholipid,
(b) 22.7 to 34.0% by weight of the polyoxyethylene coemulsifier,
(c) the lipophilic component, and
(d) 7.40 to 14.2% by weight of ethanol,
until a homogeneous clear liquid is obtained, and
(β) adding the liquid prephase obtained in step (α) to a water phase, where component (c) used in step (α), or the water phase in step (β), or both, additionally contain the lipophilic cosmetically active agent, where the total weight of lipophilic cosmetically active agent and $C_4$-$C_{18}$triglyceride of component (c) ranges from 47.6 to 56.3% by weight, and the weight ratio of total lipophilic cosmetically active agent to $C_4$-$C_{18}$triglyceride of component (c) ranges from 1.45:1 to 2.85:1.

16. A method of preparing a cosmetic formulation of a lipophilic cosmetic active agent in the form of an aqueous nanodispersion, which steps consist essentially of
(α) mixing the components
(a) 0.1 to 30% by weight of a phospholipid,
(b) 1 to 50% by weight of a polyoxyethylene coemulsifier selected from the group consisting of polyethoxylated fatty alcohols, polyethoxylated fatty acids, polyethoxylated vitamin E derivatives, polyethoxylated lanoline and lanoline derivatives, and polyethoxylated fatty acid partial glycerides,
(c) 0.1 to 80% by weight of a lipophilic component consisting of a natural or synthetic or a partially synthetic $C_4$-$C_{18}$triglyceride and a lipophilic cosmetically active agent, in which any cosmetically active agent is lipophilic and is always present in component (c), and
(d) 7.40 to 14.2% by weight of ethanol,
with conventional stirring apparatus until a homogeneous clear liquid is obtained, and
(β) adding the liquid obtained in step (α) to a water phase, wherein step (β) is carried out in the absence of high shear or cavitation forces, and wherein the average particle diameter is less than 30 nm.

17. A method according to claim 16, wherein the particles size follows a Gaussian distribution with at least 90% of the particles having a size from the range 1 to 30 nm.

18. A cosmetic composition in the form of a gel, cream, lotion, milk, a stick, a spray, an aerosol, a foam or a paste which comprises a nanodispersion as defined in claim 1.

19. A cosmetic composition comprising an aqueous phase, wherein the aqueous phase contains the nanodispersion obtained according to claim 1 in a concentration of 0.01 to 20% by weight.

20. A cosmetic composition in the form of a powder, lacquer, pellet or make-up, which comprises a nanodispersion as defined in claim 1, the nanodispersion being present in dehydrated form.

21. A nanodispersion prephase as obtained in step (α) of claim 1.

22. A cosmetic composition in the form of an oil or lacquer, which comprises a nanodispersion prephase as obtained in step (α) of claim 1.

* * * * *

UNITED STATES PATENT AND TRADEMARK OFFICE
CERTIFICATE OF CORRECTION

PATENT NO. : 7,381,423 B2  Page 1 of 1
APPLICATION NO. : 11/103208
DATED : June 3, 2008
INVENTOR(S) : Dietmar Hüglin et al.

It is certified that error appears in the above-identified patent and that said Letters Patent is hereby corrected as shown below:

<u>On Title page,</u>
Item (73) Assignee: should read:

Item -- (73) Ciba Specialty Chemicals Corp.,
Tarrytown, NY (US) and
Vesifact AG,
Baar, Switzerland --.

Signed and Sealed this

Nineteenth Day of August, 2008

JON W. DUDAS
*Director of the United States Patent and Trademark Office*